United States Patent

Rabinovich et al.

[11] Patent Number: 5,732,710
[45] Date of Patent: Mar. 31, 1998

[54] METHOD AND DEVICE FOR STABLE IMPEDANCE PLETHYSMOGRAPHY

[75] Inventors: Pavel Rabinovich, Jerusalem; Michael Shochat, Matan, both of Israel

[73] Assignee: R.S. Medical Monitoring Ltd., Jerusalem

[21] Appl. No.: 693,660

[22] Filed: Aug. 9, 1996

[51] Int. Cl.⁶ .................................................. A61B 5/05
[52] U.S. Cl. ................................. 128/734; 128/723
[58] Field of Search ........................... 128/693, 734, 128/735, 723

[56] References Cited

U.S. PATENT DOCUMENTS

| | | |
|---|---|---|
| Re. 30,101 | 9/1979 | Kubicek et al. . |
| 3,750,649 | 8/1973 | Severinghaus . |
| 3,789,834 | 2/1974 | Duroux . |
| 3,851,641 | 12/1974 | Toole et al. . |
| 3,871,359 | 3/1975 | Pacela . |
| 3,874,368 | 4/1975 | Asrican . |
| 3,971,365 | 7/1976 | Smith . |
| 4,078,553 | 3/1978 | Duroux . |
| 4,116,231 | 9/1978 | Matsuo . |
| 4,240,445 | 12/1980 | Iskander et al. . |
| 4,269,195 | 5/1981 | Itoh . |
| 4,486,835 | 12/1984 | Bai et al. . |
| 4,561,448 | 12/1985 | Buchos ................ 128/734 |
| 4,649,932 | 3/1987 | Smith . |
| 4,690,149 | 9/1987 | Ko . |
| 4,823,797 | 4/1989 | Heinze et al. . |
| 5,020,541 | 6/1991 | Marriott ................ 128/723 |
| 5,465,730 | 11/1995 | Zadehkoochak et al. . |
| 5,501,230 | 3/1996 | Laribiere . |

FOREIGN PATENT DOCUMENTS

WO 86/03391   6/1986   WIPO .

*Primary Examiner*—Francis Jaworski
*Attorney, Agent, or Firm*—Mark M. Friedman

[57] ABSTRACT

A method and device for impedance plethysmography, with relative immunity to skin-electrode contact resistance drift. Two measurement electrodes are placed on opposite sides of a biological object such as a patient. A reference electrode is placed next to one of the measurement electrodes. Because all three skin-electrode contact resistances drift in substantially the same way over time, the difference between an impedance measured between the measurement electrodes and an impedance measured between the reference electrode and the adjacent measurement electrode is indicative of a change in the biological object's impedance, even though the skin-electrode contact resistances may drift by an amount comparable to the change in the biological object's impedance.

20 Claims, 6 Drawing Sheets

METHOD AND DEVICE FOR STABLE IMPEDANCE PLETHYSMOGRAPHY

FIELD AND BACKGROUND OF THE INVENTION

The present invention relates to noninvasive medical monitoring systems and, more particularly, to a method and device for monitoring the change in time of the electrical impedance of a portion of a living body, such as the lungs or the brain, the method and the device being characterized by relative immunity to electrode drift.

Fluid buildup is associated with many diseases, notably diseases of the heart. An important example of fluid buildup associated with heart disease is acute edema of the lungs. Because these fluids are electrically conductive, changes in their volume can be detected by the technique of impedance plethysmography, in which the electrical impedance of a part of the body is measured by imposing an electrical current across the body and measuring the associated voltage difference. For example, experiments with dogs (R. V. Luepker et al., American Heart Journal, Vol. 85, No. 1, pp 83–93, January 1973) have shown a clear relationship between the transthoracic electrical impedance and the change in pulmonary fluid volume.

The monitoring of pulmonary edema using two electrodes, one either side of the biological object, is well known in the art. However, this method has proved to be unfit for prolonged monitoring due to the drift of skin-to-electrode contact layer resistance. This drift is due to ions from sweat and skin penetrating the electrolytic paste of the electrode, and the wetting of the epidermis, over the course of several hours. A method for overcoming this problem was developed by Kubicek et al. (Annals of the New York Academy of Sciences, 1970, 170(2):724–32; U.S. Pat. No. 3,340,867, reissued as Re. Pat. No. 30,101). Related U.S. patents include Asrican (U.S. Pat. No. 3,874,368), Smith (U.S. Pat. No. 3,971,365), Matsuo (U.S. Pat. No. 4,116,231) and Itoh (U.S. Pat. No. 4,269,195). The method of Kubicek et al. uses a tetrapolar electrode system whereby the outer electrodes establish a current field through the chest. The inner voltage pickup electrodes are placed as accurately as is clinically possible at the base of the neck and at the level of the diaphragm. This method regards the entire portion of the chest between the electrodes as a solid cylinder with uniform parallel current fields passing through it. However, because this system measures the impedance of the entire chest, and because a large part of the electrical field is concentrated in the surface tissues, this method is not sufficiently specific for measuring liquid levels in the lungs and has low sensitivity: 50 ml per Kg of body weight (Y. R. Berman, W. L. Schutz, Archives of Surgery, 1971.V.102:61–64). It should be noted that such sensitivity has proved to be insufficient for obtaining a significant difference between impedance values in patients without pulmonary edema to those with an edema of average severity (A. Fein et al., Circulation, 1979,60(5):1156–60). In their report on the conference in 1979 concerning measuring the change in the liquid level in the lungs (Critical Care Medicine, 1980,8(12):752–9), N. C. Staub and J. C. Hogg summarize the discussion on the reports concerning the reports on the method of Kubicek et al. for measuring thoracic bio-impedance. They conclude that the boundaries of the normal values are too wide, and the sensitivity of the method is lower than the possibilities of clinical observation and radiological analysis, even when the edema is considered to be severe. It is indicative that, in a paper six years later by N. C. Staub (Chest. 1986,90(4):588–94), this method is not mentioned at all. Other problems with this method include the burdensome nature of the two electrodes tightly attached to the neck, and the influence of motion artifacts on the impedance readings received.

Another method for measuring liquid volume in the lungs is the focussing electrode bridge method of Severinghaus (U.S. Pat. No. 3,750,649). This method uses two electrodes located either side of the thorax, on the left and right axillary regions. Severinghaus believed that part of the electrical field was concentrated in surface tissues around the thorax and therefore designed special electrodes to focus the field through the thorax. This method does not solve the problems associated with the drift in the skin-to-electrode resistance described above. An additional problem is the cumbersome nature of the large electrodes required. It is indicative that the article by Staub and Hogg, describing the 1979 conference, mentions that the focussing bridge transthoracic electrical impedance device was not discussed, despite the presence of its developer at the conference. A review by M. Miniati et al. (Critical Care Medicine, 1987,15(12):1146–54) characterizes both the method of Kubicek et al. and the method of Severinghaus as "insufficiently sensitive, accurate, and reproducible to be used successfully in the clinical setting" (p. 1146).

Toole et al., in U.S. Pat. No. 3,851,641, addresses the issue of electrode drift by measuring the impedance at two different frequencies. However, their method is based on a simplified equivalent circuit for the body in which the resistances and capacitances are assumed to be independent of frequency. Pacela, in U.S. Pat. No. 3,871,359, implicitly addresses the issue of electrode drift by measuring two impedances across two presumably equivalent parts of a body, for example, a right and a left arm or a right and a left leg, and monitoring the ratio between the two impedances. His method is not suitable for the monitoring of organs such as the lungs, which are not symmetric, or the brain, of which the body has only one. Other notable recent work in measuring the impedance of a portion of the body includes the tomographic methods and apparatuses of Bai et al. (U.S. Pat. No. 4,486,835) and Zadehkoochak et al. (U.S. Pat. No. 5,465,730). In the form described, however, tomographic methods are based on relatively instantaneous measurements, and therefore are not affected by electrode drift. If tomographic methods were to be used for long-term monitoring of pulmonary edema, they would be as subject to electrode drift problems as the other prior art methods.

There is thus a widely recognized need for, and it would be highly advantageous to have, a method and device for impedance plethysmography that is relatively immune to electrode drift over the course of several hours.

SUMMARY OF THE INVENTION

According to the present invention there is provided a method for monitoring the internal electrical impedance of a biological object, with compensation for skin-electrode resistance drift, during an extended monitoring period, comprising the steps of: (a) placing a first electrode and a second electrode on the biological object, the first electrode and the second electrode being part of a measurement circuit; (b) placing a third electrode on the biological object, substantially adjacent to the first electrode, the first electrode and the third electrode being part of a reference circuit; (c) at least twice during the monitoring period: (i) measuring a first electrical impedance of the measurement circuit, and (ii) measuring a second electrical impedance of the reference circuit.

According to the present invention there is provided a method for monitoring the internal electrical impedance of a biological object, with compensation for skin-electrode resistance drift, during an extended monitoring period, comprising the steps of: (a) placing a first electrode and a second electrode on the biological object, the first electrode and the second electrode being part of a measurement circuit; (b) placing a third electrode on the biological object, substantially adjacent to the first electrode, the first electrode and the third electrode being part of a reference circuit; (c) imposing an alternating electrical current between the first electrode and the second electrode; (d) imposing the alternating electrical current between the first electrode and the third electrode; and (e) at least twice during the monitoring period: (i) obtaining a first voltage signal representative of a voltage difference in the measurement circuit, and (ii) obtaining a second voltage signal representative of a voltage difference in the reference circuit.

According to the present invention there is provided an impedance plethysmography device, comprising: (a) a first electrode; (b) a second electrode; (c) a third electrode; (d) a measurement electrical circuit including the first electrode, the second electrode, and a first impedance measurement means for measuring a first electrical impedance; and (e) a reference electrical circuit including the first electrode, the third electrode, and a second impedance measurement means for measuring a second electrical impedance.

According to the present invention there is provided a medical monitoring system comprising an impedance plethysmography device, the impedance plethysmography device further comprising: (a) a first electrode; (b) a second electrode; (c) a third electrode; (d) a measurement electrical circuit including the first electrode, the second electrode, and a first impedance measurement means for measuring a first electrical impedance; and (e) a reference electrical circuit including the first electrode, the third electrode, and a second impedance measurement means for measuring a second electrical impedance.

The present invention is a method and device for monitoring the electrical impedance of a biological object such as a living body for an extended period of time, where the term "extended" is used herein to mean at least as long as the time over which electrode drift changes the skin-electrode contact resistance by an amount comparable to the anticipated change in the impedance of the biological object itself. Examples of the use of the invention in a hospital setting include the monitoring of pulmonary edema and cerebral edema. Fluid builds up in the lungs and brain, respectively, to a level detectable by the present invention sooner than clinical symptoms appear. Therefore, a patient to whom the device of the present invention is attached may be monitored remotely for pulmonary edema or cerebral edema, and appropriate therapies may be initiated much earlier than if only clinical symptoms are relied on, with a consequent reduction of mortality and morbidity.

The present invention is based on two physical assumptions. The first assumption is that the total impedance measured across two electrodes placed on opposite sides of the biological object is the sum of two impedances: the impedance of the skin-electrode contacts and the impedance of the body. The second assumption is that all skin-electrode contacts drift to the same degree in the same amount of time. According to the present invention, two measurement electrodes are placed on opposite sides of the biological object, and a third, reference electrode is placed next to one of the measurement electrodes. The impedance measured between the measurement electrodes is a sum of the impedance of the biological object and a skin-electrode contact impedance. The impedance measured between the reference electrode and the adjacent measurement electrode is substantially only the skin-electrode contact impedance and the skin impedance. Therefore, subtracting the impedance measured between the reference electrode and the adjacent measurement electrode from the impedance measured between the two measurement electrodes yields a corrected impedance whose change over time accurately reflects the change over time of the impedance of the biological object. A persistent decrease in the corrected impedance may be indicative of a buildup of electrically conductive fluid in the body.

Reference electrodes have been used before in a biomedical context, notably by Laribiere (U.S. Pat. No. 5,501,230). However, Laribiere uses a reference electrode for a purpose different from its use in the present invention. Laribiere's reference electrode is used in a circuit that detects when one of two signal measuring electrodes becomes detached from the skin of a patient.

Most conveniently, the impedance measurements of the present invention are performed by imposing alternating current from the same current source on both the measurement circuit (the circuit that includes the two measurement electrodes) and the reference circuit (the circuit that includes the reference electrode and the adjacent measurement electrode). Because both circuits have the same current, voltage drops measured between the electrodes serve as proxies for the impedances themselves. Preferably, a balancing means is provided to equalize the voltage drops across the two circuits at the beginning of a monitoring period. This balancing means may be a variable resistor in series with the electrodes in the reference circuit. At the beginning of a monitoring period, the balancing means is adjusted so that the voltage drops across the two circuits are substantially equal. As fluid builds up, the difference between the two voltage drops increases. When this difference exceeds a threshold, an emergency condition is signalled, for example by an audible alarm.

In other embodiments of the present invention, the balancing means is not used. Instead, signal processing circuitry is provided that digitizes the voltage drops, subtracts the voltage drop across the measurement circuit from the voltage drop across the reference circuit, and, at the beginning of a monitoring period, stores the initial value of that difference. That initial value is subtracted from subsequently measured values of that difference to provide a second difference. When the second difference exceeds a threshold, an emergency condition is signalled.

The scope of the present invention includes the device of the present invention both as an independent device and as a component of a more general medical monitoring system. Such a monitoring system may also include a pulmonary monitor or an ECG.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and device for monitoring the electrical impedance of a living body. Specifically, the present invention can be used to monitor a patient for signs of edema, for example pulmonary edema or cerebral edema.

The principles and operation of a monitoring system according to the present invention may be better understood with reference to the drawings and the accompanying description.

Figure 1:
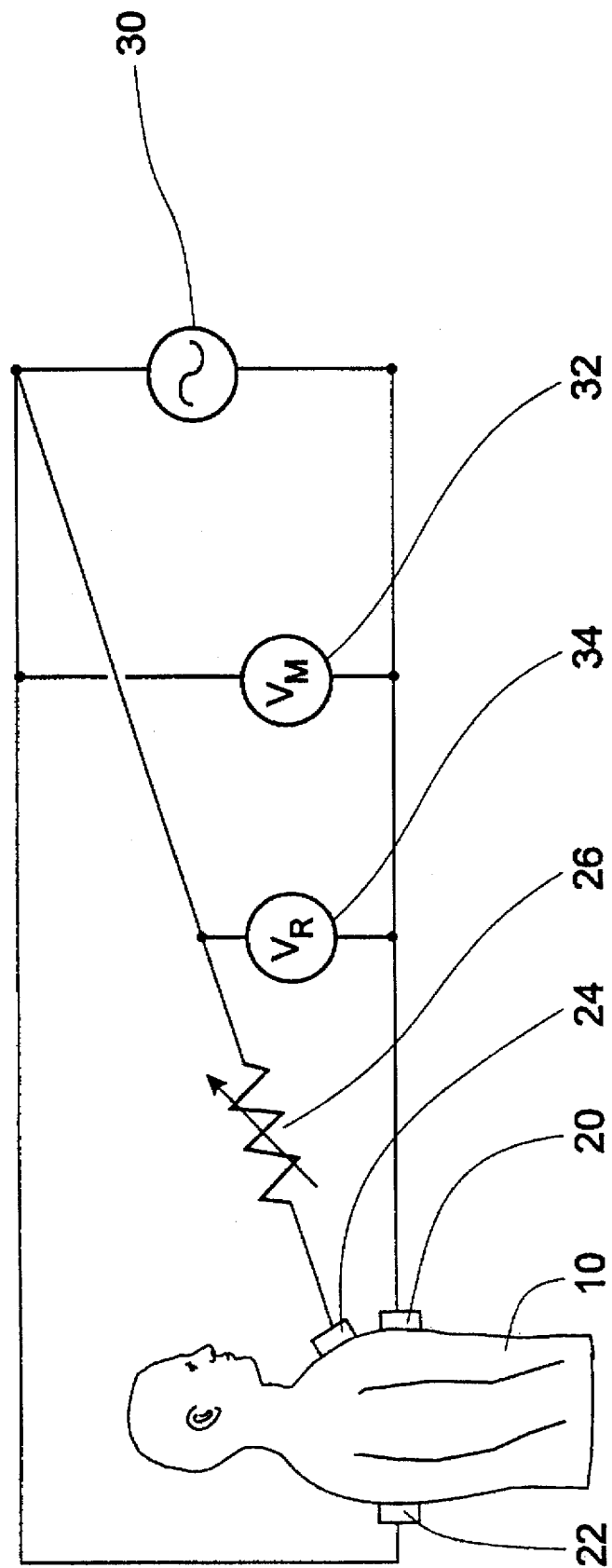
FIG. 1 is a schematic illustration of a preferred embodiment of the device of the present invention as used to monitor pulmonary edema.

Referring now to the drawings, FIG. 1 illustrates the circuitry of a preferred embodiment of the device of the present invention as used to monitor pulmonary edema. A first measurement electrode 20 and a second measurement electrode 22 are placed on opposite sides of the thorax of a patient 10. Electrode 20 is placed at the point of intersection of the 4-intercostal space and the medroclavicular line of patient 10. Electrode 22 is placed on the back of patient 10, opposite electrode 20. A reference electrode 24 is placed on the thorax of patient 10 close to electrode 20. A source 30 of alternating current supplies electrical current to the electrodes as shown. Preferably, source 30 supplies between about 4 mA and about 10 mA of current at a frequency of between about 50 Khz and about 200 Khz. The term "frequency", as used herein, refers to the fundamental frequency of a periodic waveform, so that the scope of the present invention includes alternating current of any periodic waveform, for example square waves, and not just sinusoidally varying alternating current. A variable resistor 26 is in series with reference electrode 24. Patient 10, electrodes 20 and 22, and current source 30 comprise a measurement circuit. Patient 10, electrodes 20 and 24, variable resistor 26, and current source 30 comprise a reference circuit. Voltage measurement means 32 and 34 are provided for measuring the voltage drop $V_M$ across the measurement circuit, and the voltage drop $V_R$ across the reference circuit, respectively.

It is to be understood that the preferred embodiment of FIG. 1 is illustrative. In particular, the scope of the present invention is not restricted to circuitry in which voltage drops across the measurement circuit and the reference circuit are measured explicitly, but rather includes all circuitry which accomplishes the ends of the method of the present invention, using signals representative of the voltage drops $V_M$ and $V_R$.

At the beginning of a monitoring session, variable resistor 26 is adjusted so that $V_M$ and $V_R$ are substantially equal. Subsequently, $V_M$ and $V_R$ are monitored periodically, preferably automatically. Because the skin-electrode contacts of electrodes 20, 22, and 24 are substantially identical, a substantial drop of $V_M$ below $V_R$ is indicative of a drop of the electrical impedance of the thorax of patient 10, and therefore of the onset of pulmonary edema in patient 10, even at times greater than the time over which the skin-electrode contact resistance changes by an amount comparable to the change in the impedance of the thorax of patient 10 caused by the onset of pulmonary edema.

Figure 2:
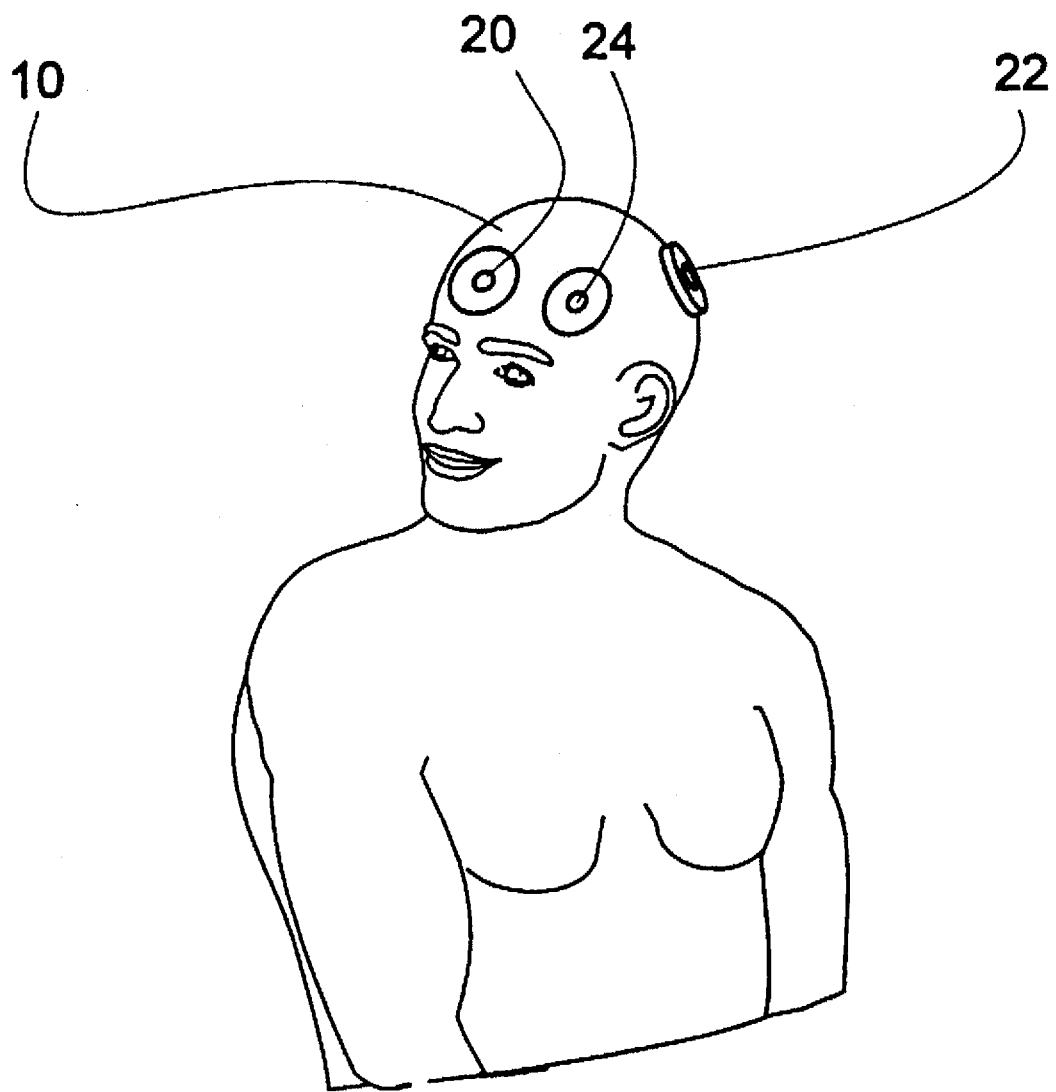
FIG. 2 is a partial schematic illustration of the use of the device of the present invention to monitor cerebral edema.

FIG. 2 shows how electrodes 20, 22, and 24 are placed on the head of patient 10 for monitoring cerebral edema. Measurement electrodes 20 and 22 are placed on opposite sides of the head of patient 10, and reference electrode 24 is placed next to electrode 20. Electrodes 20, 22, and 24 are connected to the circuitry of the device of the present invention just as in the monitoring of pulmonary edema depicted in FIG. 1.

Figure 3:
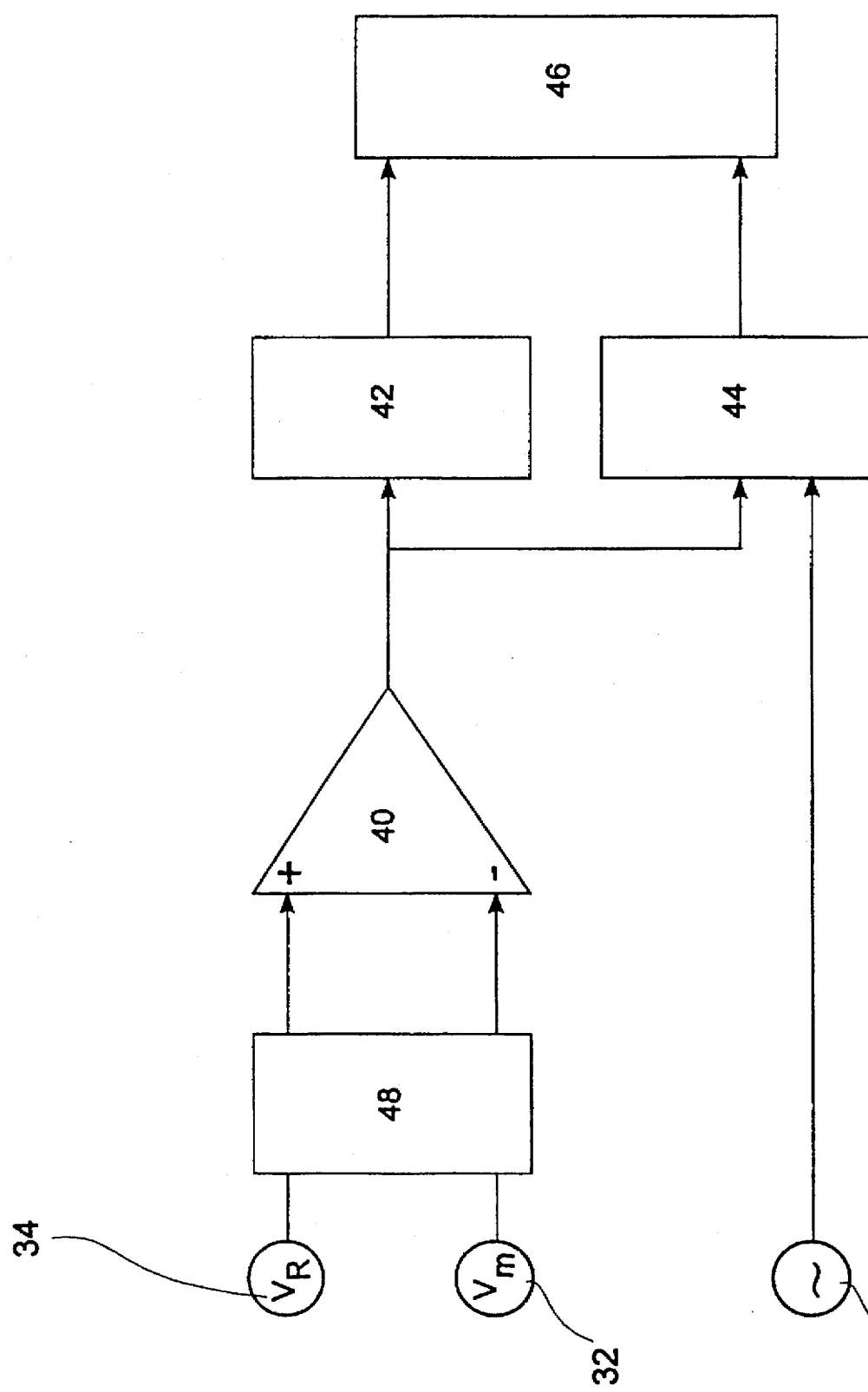
FIG. 3 is a schematic block diagram of the signal processing in a preferred embodiment of the device of the present invention.

FIG. 3 is a schematic block diagram of the signal processing in an exemplary embodiment of the present invention. A signal from voltage measurement means 32 representing $V_M$ is phase locked with a signal from voltage measurement means 34 representing $V_R$ in a suitable phase lock means 48. The signal representing $V_M$ then is subtracted from the signal representing $V_R$ in a suitable subtraction means 40, for example, an operational amplifier, to provide a difference signal. This difference signal is input to an amplitude measurement means 42 and a phase detection means 44. Amplitude measurement means 42 measures the amplitude of the difference signal. Phase detection means 44 measures the phase difference between the difference signal and a reference signal from current source 30. The amplitude and the phase difference are input to a display means 46, which displays the values of the amplitude of the difference signal and its phase relative to current source 30.

Figure 4A:
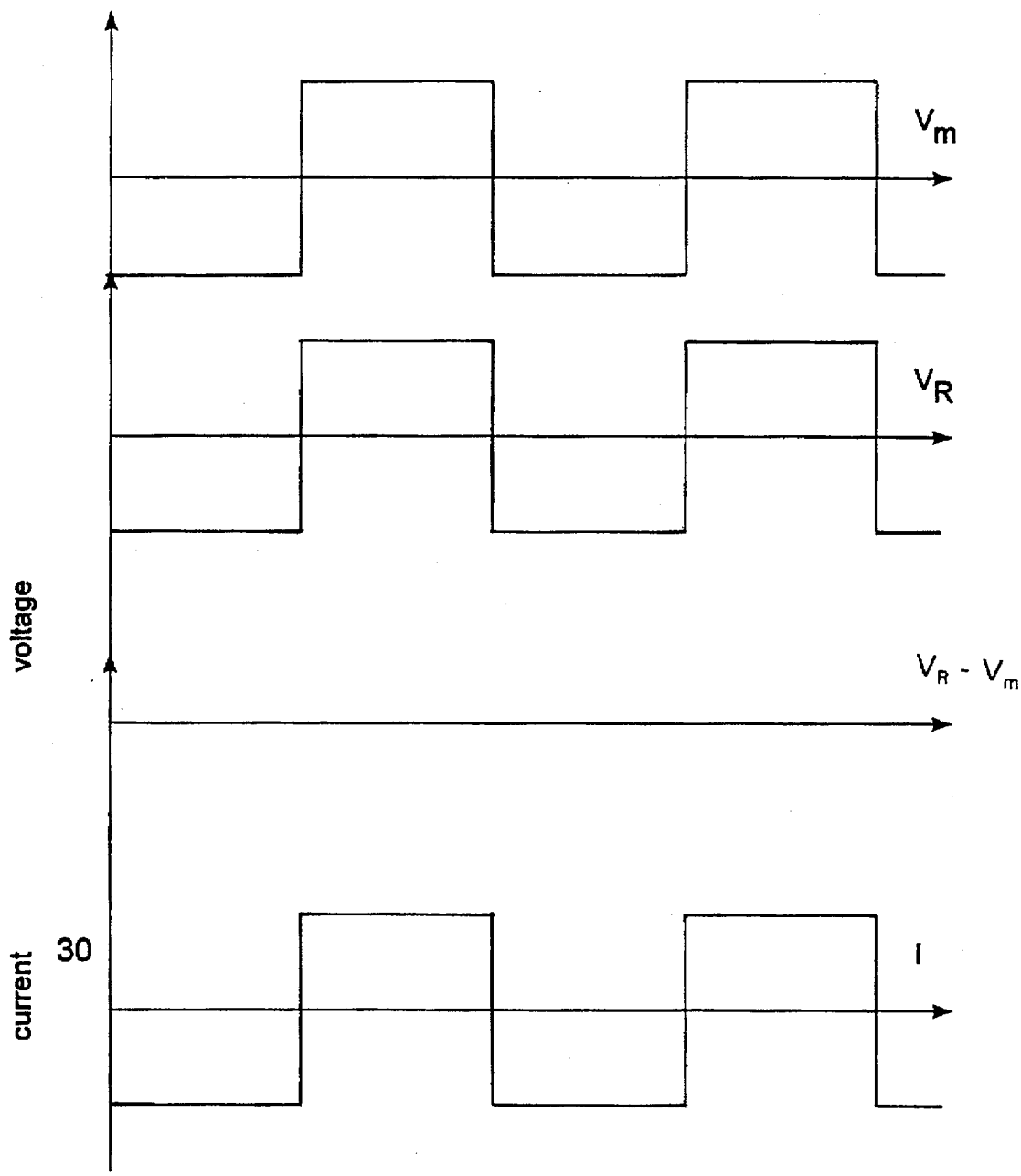
FIG. 4A is a schematic plot of the voltages and the current at the start of monitoring.
Figure 4B:
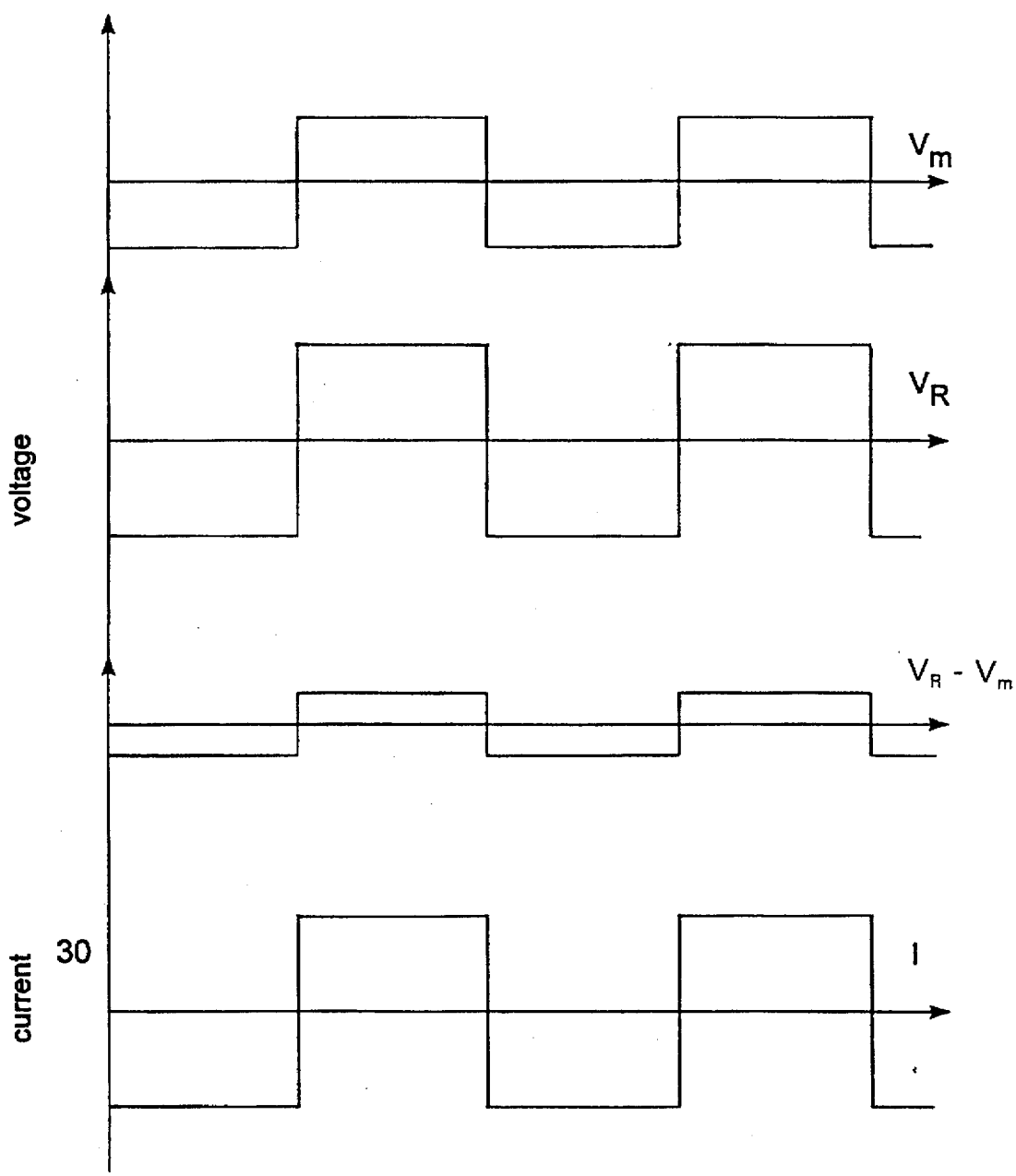
FIG. 4B is a schematic plot of the voltages and the current at the onset of significant fluid buildup.
Figure 4C:
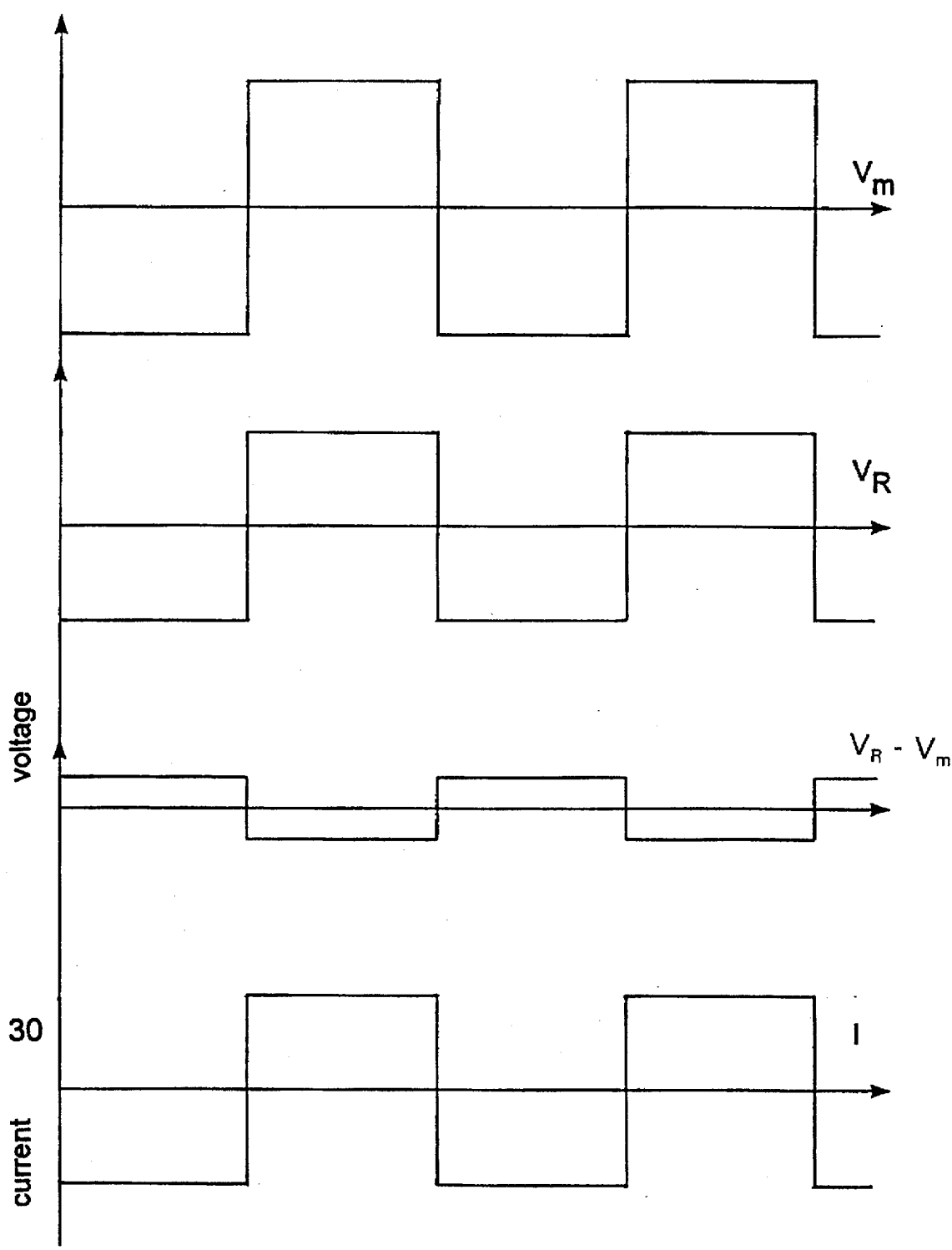
FIG. 4C is a schematic plot of the voltages and the current at the onset of significant fluid decrease.

FIGS. 4A, 4B and 4C show schematic plots of the alternating current I supplied by current source 30, and the resulting voltage drops and difference signal, as functions of time. The wave form of alternating current I shown in FIGS. 4A, 4B and 4C is a square wave. FIG. 4A shows the situation at the start of monitoring. Both $V_M$ and $V_R$ are substantially in phase with current I. Because the biological object has both an equivalent resistance and an equivalent capacitance, voltage drops $V_M$ and $V_R$ can not be exactly in phase with each other; but phase locking means 48 is used to synchronize the phases of the signals representative of $V_M$ and $V_R$, so that a suitable adjustment of variable resistor 26 substantially nulls the difference signal produced by subtraction means 40 and labeled in FIG. 4A as "$V_R-V_M$". FIG. 4B shows the situation at the onset of significant fluid buildup. I is the same in FIG. 4B as in FIG. 4A. Because of electrode drift, $V_R$ in FIG. 4B is similar, but not identical, to $V_R$ in FIG. 4A. Because of the buildup of electrically conductive fluid, $V_M$ is smaller in amplitude in FIG. 4B than in FIG. 4A. Therefore, the difference signal "$V_R-V_M$" has a significant amplitude in FIG. 4B, and is substantially in phase with the current I. If the amplitude of the difference signal exceeds a threshold, display means 46 compares the phases of the difference signal and the current I. If the difference signal is in phase with the current I, then the large amplitude is indicative of a buildup of fluid, and display means 46 triggers an alarm.

FIG. 4C shows the situation at the onset of significant fluid decrease. I is the same in FIG. 4C as in FIGS. 4A and 4B. As in FIG. 4B, $V_R$ in FIG. 4C is similar, but not identical to, $V_R$ in FIG. 4A because of electrode drift. Because of the decrease in electrically conductive fluid, $V_M$ is larger in amplitude in FIG. 4C than in FIG. 4A. As in FIG. 4B, the difference signal "$V_R-V_M$" has a significant amplitude in FIG. 4C. Unlike the difference signal in FIG. 4B, the difference signal in FIG. 4C is substantially out of phase with the current I.

While the invention has been described with respect to a limited number of embodiments, it will be appreciated that many variations, modifications and other applications of the invention may be made.

What is claimed is:

1. A method for monitoring the internal electrical impedance of a biological object, with compensation for skin-electrode resistance drift, during an extended monitoring period, comprising the steps of:

(a) placing a first electrode and a second electrode on the biological object, said first electrode and said second electrode being part of a measurement circuit;

(b) placing a third electrode on the biological object, substantially adjacent to said first electrode, said first electrode and said third electrode being part of a reference circuit;

(c) at least twice during the monitoring period:
  (i) measuring a first electrical impedance of said measurement circuit, and
  (ii) measuring a second electrical impedance of said reference circuit.

2. The method of claim 1, further comprising the step of: at least twice during the monitoring period, subtracting said first electrical impedance from said second electrical impedance, thereby providing an impedance difference.

3. The method of claim 2, further comprising the step of: if said impedance difference exceeds a threshold: initiating an emergency procedure.

4. The method of claim 2, further comprising the steps of:
  (a) providing a balancing means in said reference circuit; and
  (b) adjusting said balancing means so that, at a first measurement of said first electrical impedance and of said second electrical impedance, said first electrical impedance substantially equals said second electrical impedance.

5. The method of claim 4, wherein said balancing means includes at least one variable resistor.

6. A method for monitoring the internal electrical impedance of a biological object, with compensation for skin-electrode resistance drift, during an extended monitoring period, comprising the steps of:
  (a) placing a first electrode and a second electrode on the biological object, said first electrode and said second electrode being part of a measurement circuit;
  (b) placing a third electrode on the biological object, substantially adjacent to said first electrode, said first electrode and said third electrode being part of a reference circuit;
  (c) imposing an alternating electrical current between said first electrode and said second electrode;
  (d) imposing said alternating electrical current between said first electrode and said third electrode; and
  (e) at least twice during the monitoring period:
    (i) obtaining a first voltage signal representative of a voltage difference in said measurement circuit, and
    (ii) obtaining a second voltage signal representative of a voltage difference in said reference circuit.

7. The method of claim 6, further comprising the step of: at least twice during the monitoring period: subtracting said first voltage signal from said second voltage signal, thereby providing a difference signal having an amplitude.

8. The method of claim 7, further comprising the steps of:
  (a) providing a balancing means in said reference circuit; and
  (b) adjusting said balancing means so that, at a first measurement of said first voltage signal and of said second voltage signal, said first voltage signal substantially equals said second voltage signal.

9. The method of claim 8, wherein said balancing means includes at least one variable resistor.

10. The method of claim 8, further comprising the steps of:
  (a) providing means for phase locking said first voltage signal and said second voltage signal; and
  (b) phase locking said first voltage signal and said second voltage signal, thereby substantially nulling said difference signal at said first measurement.

11. The method of claim 10, further comprising the step of: if said amplitude exceeds a threshold and said difference signal is in phase with said alternating electrical current: initiating an emergency procedure.

12. The method of claim 8, further comprising the step of: if said amplitude exceeds a threshold and said difference signal is in phase with said alternating electrical current: initiating an emergency procedure.

13. An impedance plethysmography device, comprising:
  (a) a first electrode;
  (b) a second electrode;
  (c) a third electrode;
  (d) a measurement electrical circuit including said first electrode, said second electrode, and a first impedance measurement means for measuring a first electrical impedance; and
  (e) a reference electrical circuit including said first electrode, said third electrode, and a second impedance measurement means for measuring a second electrical impedance.

14. The device of claim 13, wherein said first impedance measurement means and said second impedance measurement means share a common source of alternating electrical current.

15. The device of claim 14, wherein said alternating electrical current has a frequency of between about 50 Khz and about 200 Khz, and wherein said alternating electrical current has a current level of between about 4 mA and about 10 mA.

16. The device of claim 14, wherein said reference electrical circuit includes a balancing means, said device further comprising:
  (a) subtraction means for subtracting said first electrical impedance from said second electrical impedance, thereby providing a difference signal having an amplitude;
  (b) amplitude measurement means for measuring said amplitude of said difference signal; and
  (c) phase detection means for detecting a phase difference between said alternating electrical current and said difference signal.

17. The device of claim 16, further comprising phase locking means for phase locking said first electrical impedance and said second electrical impedance.

18. The device of claim 17, further comprising an alarm responsive to said amplitude measurement means and to said phase detection means.

19. The device of claim 16, further comprising an alarm responsive to said amplitude measurement means and to said phase detection means.

20. A medical monitoring system comprising an impedance plethysmography device, said impedance plethysmography device further comprising:
  (a) a first electrode;
  (b) a second electrode;
  (c) a third electrode;
  (d) a measurement electrical circuit including said first electrode, said second electrode, and a first impedance measurement means for measuring a first electrical impedance; and
  (e) a reference electrical circuit including said first electrode, said third electrode, and a second impedance measurement means for measuring a second electrical impedance.

* * * * *